United States Patent [19]
Evans et al.

[11] Patent Number: 5,020,368
[45] Date of Patent: Jun. 4, 1991

[54] METHOD AND SYSTEM MEASURING A VERTICAL DENSITY PROFILE OF A FLUID

[75] Inventors: Peter G. Evans; John B. Cole, both of Ince, Great Britain

[73] Assignee: Shell Oil Company, Houston, Tex.

[21] Appl. No.: 441,502

[22] Filed: Nov. 27, 1989

[30] Foreign Application Priority Data

Nov. 30, 1988 [GB] United Kingdom ............... 8827901

[51] Int. Cl.$^5$ ............................................. G01N 9/28
[52] U.S. Cl. ...................................... 73/439; 73/299; 73/438; 73/302
[58] Field of Search .................. 73/299, 438, 439, 302

[56] References Cited

U.S. PATENT DOCUMENTS

| | | | |
|---|---|---|---|
| 3,422,682 | 1/1969 | Evans et al. | 73/438 |
| 3,460,394 | 8/1969 | Cryer | 73/439 |
| 3,613,456 | 10/1971 | Hopfe et al. | 3/439 |
| 3,620,085 | 11/1971 | Khoi | 73/439 |
| 4,006,635 | 2/1977 | Khoi | 73/299 |
| 4,307,609 | 12/1981 | Rosenblum | 73/438 |
| 4,425,787 | 1/1984 | Saraf | 73/32 |
| 4,471,656 | 9/1984 | Sanders et al. | 73/438 |
| 4,625,553 | 12/1986 | Carter | 73/438 |
| 4,630,478 | 12/1986 | Johnson | 73/299 |

FOREIGN PATENT DOCUMENTS

| | | |
|---|---|---|
| 0048589 | 3/1987 | European Pat. Off. . |
| 395063 | 5/1921 | Fed. Rep. of Germany . |
| 1082066 | 12/1954 | France . |
| 0201532 | 8/1988 | Japan ................ 73/299 |

*Primary Examiner*—Hezron E. Williams
*Assistant Examiner*—Craig Miller
*Attorney, Agent, or Firm*—Ronald R. Reper

[57] ABSTRACT

Method and system for measuring vertical density profile of fluid by pressurizing an array of pipes, determining level and pressure signals on each pipe and deriving profile therefrom.

8 Claims, 1 Drawing Sheet

METHOD AND SYSTEM MEASURING A VERTICAL DENSITY PROFILE OF A FLUID

BACKGROUND OF THE INVENTION

The present invention relates to a method for measuring a vertical density profile of a fluid in a fluid storage tank.

Particularly the present invention relates to a method, a system and a fluid level sensor head for measuring vertical density profiles in a Liquified Natural Gas (LNG) tank.

In an LNG tank the phenomenon of "roll-over" is a potential cause of damage to such tanks. The phenomenon of "roll-over" should be understood as an uncontrolled rising of a superheated fluid layer from the bottom of such a tank, accompanied by rapid vaporization which may overwhelm the tank pressure relief systems. Hereinafter this phenomenon will be described in more detail.

When an LNG cargo is loaded into a tank, underneath already stored LNG, stratification can occur if the cargo is more dense than the original contents. Over a period of time, heat leaking into the tank bottom and the boiling-off of the lighter components at the surface, may cause the densities of the two layers to become equal before the temperatures of the layers come into equilibrium. Convection currents, previously restricted to the separate strata because of the density difference, can now occur throughout the whole tank. As stated above the bottom layer can rise to the surface, accompanied by rapid vaporisation which may overwhelm the tank pressure relief systems with hazardous consequences. Knowledge of the vertical temperature and density profiles can provide operators with information on whether the prevailing conditions may lead to roll-over, so that appropriate operational procedures can be applied.

A conventional method applied in this field is the "bubbler" or gas purge method which comprises the step of measuring hydrostatic pressure, commonly used in the determination of liquid level and density in ambient temperature products. Gas is allowed to bubble through an open-ended tube at a known height in the liquid and a pressure transducer mounted outside the tank measures the gas pressure required to produce the bubbles. This conventional method is not very accurate, because the vertical position corresponding to the measured pressure is ill-defined and depends on the variable mechanism of bubble release.

Thus it is an obJect of the invention to provide an improved method, a system and a fluid level sensor head for measuring a vertical density profile wherein the measurements are made with high accuracy.

Another object of this invention is to provide a method, a system and a fluid level sensor head for measuring a vertical density profile which does not disturb the conditions present in the fluid to be investigated, for example LNG.

SUMMARY OF THE INVENTION

The invention therefore provides a method for measuring a vertical density profile of a fluid in a fluid storage tank by means of an array of open ended pressure pipes extending downward into said fluid, the top end of each pressure pipe being connectable to a common pressurizing gas supply and the bottom end incorporating a fluid level sensor head, the method comprising the following steps, carried out for each pipe:

connecting said pipe with the common gas supply, conducting the pressurizing gas into said pipe thereby forcing the fluid downward into said fluid level sensor head, comprising a lower end part in which the fluid passes an outlet opening forming an abrupt transition between said lower end part and an open ended tube, determining a level indicating signal from the passing fluid, determining a pressure indicating signal from the pressure on the fluid, and deriving from said level and pressure indicating signals information on the said vertical density profile.

The invention further provides a system for measuring a vertical density profile of a fluid in a fluid storage tank by means of an array of open ended pressure pipes, extending downward into said fluid, the top end of each pressure pipe being connectable to a common pressurizing gas supply, and the bottom end incorporating a fluid level sensor head, the system comprising for each pipe:

means for connecting said pipe with the common gas supply, means for conducting the pressurizing gas into said pipe thereby forcing the fluid downward into said fluid level sensor head, comprising a lower end part in which the fluid passes an outlet opening forming an abrupt transition between said lower end part and an open ended tube, means for determining a level indicating signal from the passing fluid, means for determining a pressure indicating signal from the pressure on the fluid, and means for deriving from said level and pressure indicating signals information on the said vertical density profile.

The invention also provides a fluid level sensor head comprising an inlet opening, connected with a pressure pipe as a conduit for fluid forced downward by means of a pressurizing gas, and a lower end part, provided with an outlet opening forming an abrupt transition between said lower end part and an open ended tube.

Advantageously the lower end part of the fluid level sensor head is a tube with a diameter substantially greater than the diameter of the open ended tube. Particularly the outlet opening is comprised of a flat bottom connecting the lower end part with the open ended tube and normal to the axes of said tubes. In a further detail the lower end part is a tubular room the inlet opening of which has a diameter smaller than the diameter of the tubular room.

BRIEF DESCRIPTION OF THE DRAWINGS

The invention will now be described by way of example in more detail with reference to the accompanying drawings, wherein FIG. 1 schematically shows a system for measuring a vertical density profile of a fluid in a fluid storage tank in accordance with the invention.

DESCRIPTION OF PREFERRED EMBODIMENTS

Figure 1:
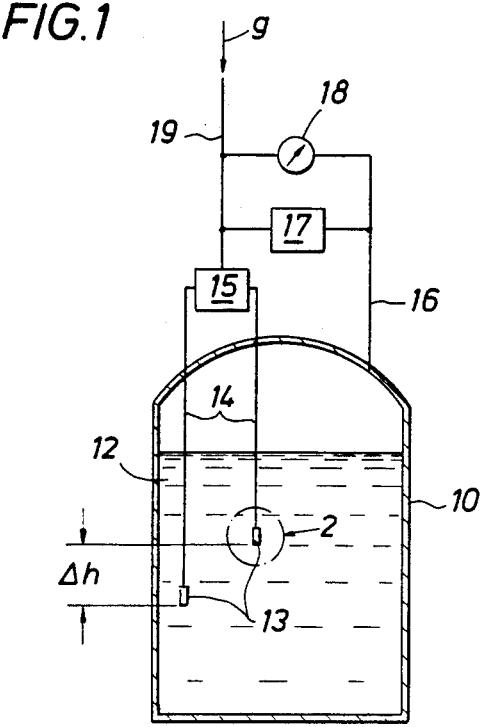

In the figures the same reference numerals are used to indicate the same or similar parts or components.

Referring to FIG. 1 a schematic overview of the system is shown in accordance with the present invention. In a fluid storage tank 10 a fluid 12 is contained of which a vertical density profile has to be determined. If for example the fluid 12 is LNG there may be a potential risk, as stated above, of the phenomenon of "rollover" occurring during storage. For reasons of clarity only an array of two fluid level sensor heads 13 is shown. It is noted that an array may consist of many more sensor heads 13 when a complete profile has to be determined. Each sensor head 13 is mounted in any suitable manner on a pressure pipe 14 through which a pressurizing gas, for example He (helium) or $N_2$ (nitrogen), flows to force the fluid down thereby lowering the fluid level. In the case of LNG helium was chosen to be the working gas because of its low solubility in LNG, although nitrogen would be acceptable and more economical for normal use. When said level reaches the respective sensor head an accurate level value will be obtained as will be explained below.

To calculate a mean density value, data is needed from a pair of sensor heads. The fluid level measurements are made separately with each sensor head, a selector valve 15 selecting the appropriate sensor head from said array.

The system further comprises a vent pipe 16 extending from the top of the storage tank 10, a vent valve 17 to reduce the pressure of the gas in a gas supply pipe 19, and a pressure transducer 18 conventionally used in order to measure differential pressure. The direction of the pressurizing gas flow in the supply pipe 19 is indicated by the arrow g.

As can be seen in FIG. 1 the height difference between such a pair of sensor heads 13 has a set value $\Delta h$. Furthermore the heights (or depths) of the sensor heads, particularly of the level indicating components, are preset exactly. Then by means of equations for hydrostatic equilibrium which are known to those skilled in the art and will not be described in detail the mean density value of such a $\Delta h$ layer can be calculated using gas and gravity characteristics as required.

Figure 2:
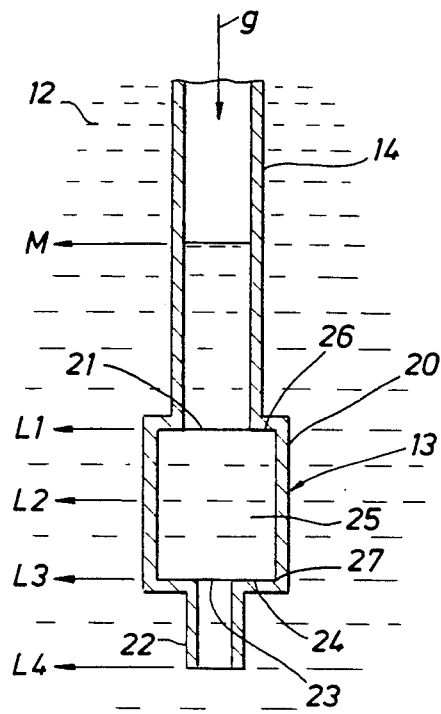
FIG. 2 is a detail 2 of FIG. 1 drawn on a scale larger than the scale of FIG. 1 and gives a cross-sectional view of an advantageous embodiment of a fluid level sensor head in accordance with the invention.

FIG. 2 as a detail 2 of FIG. 1, drawn on a scale larger than the scale of FIG. 1, shows a cross-sectional view of an advantageous embodiment of a fluid level sensor head 13 in accordance with the present invention. The sensor head 13 is connected with a gas pressure pipe and extends into the fluid filled storage tank. The fluid 12 is forced downward into the pressure pipe 14 by the pressurizing gas as indicated by the arrow g, the fluid having a fluid level or surface M. Said level M will be lowered further by said pressurizing gas in that the fluid level M will pass four successive levels, indicated respectively L1-L4.

As shown in this figure the sensor head 13 comprises a lower end part 20 with an inlet opening 21 at level L1 and provided with an outlet opening 23 at level L3, the outlet opening 23 forming an abrupt transition between said lower end part 20 and an open ended tube 22. At level L3 the cross-sectional area of the sensor head is reduced substantially.

Advantageously the lower end part 20 is a tube with a diameter substantially greater than the diameter of the open ended tube 22.

In the embodiment of the fluid level sensor head 13 as shown in this figure the outlet opening 23 is comprised in a flat bottom 24 connecting the lower end part 20 with the open ended tube 22 and normal to the axes of said tubes. Furthermore the inlet opening 21 of the lower end part 20 has a diameter smaller than the diameter of said lower end part, thus forming a tubular room 25 between the pressure pipe 14 and the open ended tube 22 thus allowing a more abrupt transition at level L3. As can be seen also in FIG. 2 the inlet opening 21 is comprised in a flat top 26 connecting the tubular room 25 with the pressure pipe 14 and normal to the axes of said room and pipe. In said embodiment the pressure pipe 14, the lower end part 20 and the open ended tube 22 are arranged coaxially. However, such an arrangement is not necessary as will be clear to those skilled in the art.

In an advantageous embodiment the junction between the lower end part 20 and the flat bottom 24 can be curved to assist the fluid to drain smoothly as its surface passes into the outlet opening 23.

Figure 3:
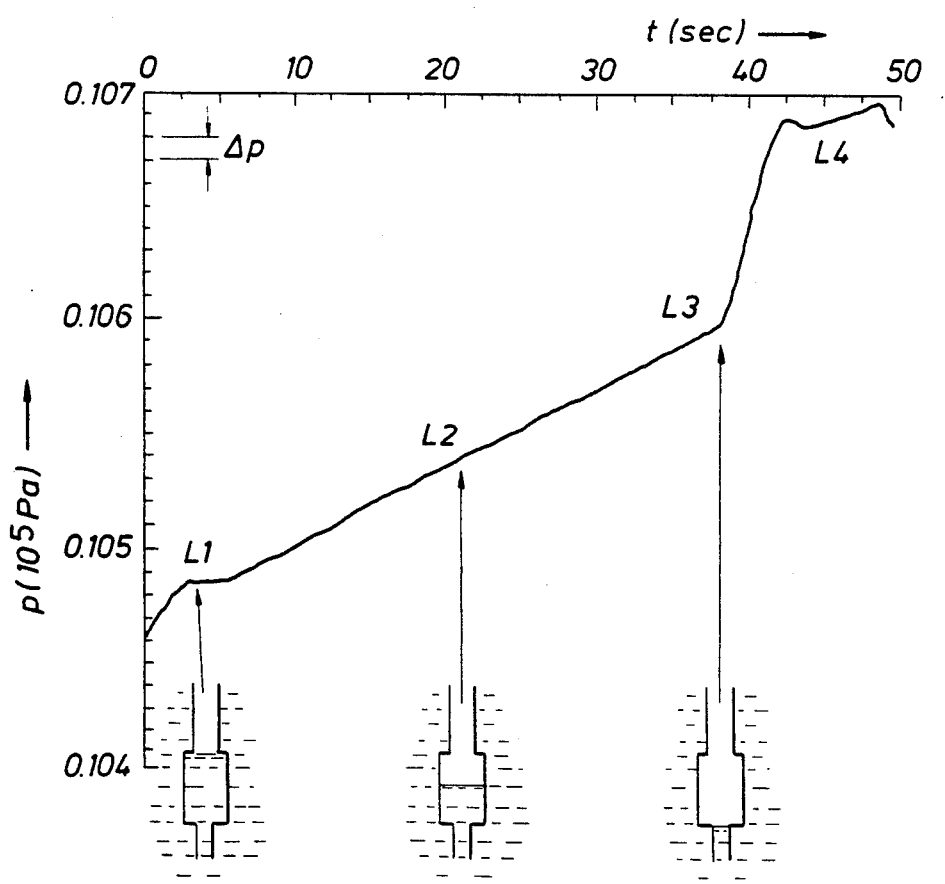
FIG. 3 is a plot showing a curve as measured for LNG using the fluid level sensor head of the present invention during an operating cycle.

Referring to FIG. 3 a plot is shown illustrating the pressure behaviour of LNG within the sensor head in accordance with the invention during the lowering of the fluid surface M. The sensor head used for the measurements of the FIG. 3 plot did have internal diameters of 12.0 mm, 22.10 mm and 5 mm, respectively, for the pressure pipe 14, the lower end part 20 and the open end part 22 and an internal height for said end part of 29 mm. Pressure readings from the pressure transducer 18 are measured at known time intervals and are plotted, with pressure on the vertical axis and time t on the horizontal axis, respectively in units $10^5$ Pa and s. A pressure unit is marked by $\Delta p$ corresponding to the pressure of 2.2 mm of LNG when the density p is 460 kg/$m^3$. Also indicated on the plot are the said four sensor head levels, L1, L2, L3 and L4. As shown in the plot the passing of a cross-sectional area transition (sensor head levels L1, L3 and L4) by the fluid surface is significantly resolved as a sharp discontinuity in the rate of change of pressure. Particularly passing of level L3, at the outlet opening 23 as shown in FIG. 2 is marked clearly. Thus a precise measurement of pressure at each level is obtained. Consequently accurate average density values as described hereinbefore can be calculated.

It is noticed that the sharpness of the discontinuity will be influenced by various factors. Among these, flow rate of the downward pressurized fluid, viscosity of the fluid, and ratio of diameters (or cross-sectional areas) of the lower end part and the outlet opening to the open ended tube will be of great importance. Therefore, the choosing of suitably compatible dimensions, magnitudes and properties will be the result of engineering practice.

The measurement sequence is as follows: a sensor head is selected and the mean pressure required to produce bubbles at the open end of the sensor head determined. This pressure value is used as a reference to preset the fluid surface within the sensor head. As an alternative the detection of level L1 can be used as a source of reference pressure to preset the fluid surface and in this case no bubbles need be evolved into the main body of the fluid. Pressure readings are then taken at equal time intervals, and for example plotted on a computer screen and stored. Advantageously at the same time the pressure rate is calculated in order to determine when the fluid surface is traversing the restriction. A fixed number of data points are collected after the detection of the discontinuity. The sequences of pressure measurements are then analysed, to determine the precise pressure at the discontinuity L3 in the plot, i.e. the abrupt change of gradient.

For example, the following algorithm is used. A window, 80 samples wide, is selected, a straight line is fitted to the points by a least squares method and the standard deviation of the pressure readings about the line is determined. The window is stepped through the data sequence, a new line being determined at each step, until a position is found where both (i) the next five points beyond the window lie above the fitted line by more than two standard deviations and (ii) the sixth point by more than four standard deviations. The last point in the window is then taken to be the one nearest to the transition. A second line is fitted to the next 25 points following the transition and the exact pressure at the discontinuity is determined as the intersection of the two fitted lines. Subsequent sensor heads from said array are then selected in turn and the pressures at their discontinuities determined. The density profile is then calculated.

It will be clear to those skilled in the art that various refinements can be incorporated in effecting the measurement sequence. For example the pressure transducer readings can be compensated for temperature drift by periodically connecting both pressure ports to the tank vapour space and then measuring the output. Such reference values can be used for calibration corrections.

Furthermore two gas flow rates can be used, a high flow to quickly move the fluid level within the selected tube and a low flow for use during the measurements. Also the position of the fluid level within the tube can be preset by using a combination of venting to the vapour space to raise it and the gas flow to depress it.

It will be appreciated that the measurement and control system will consist of advanced measuring and control means, such as programmable switch units, digital multimeters and solenoid valves, controlled by means of a computer system enabling automated operation.

Various modifications of the present invention will become apparent to those skilled in the art from the foregoing description and accompanying drawings. Such modifications are intended to fall within the scope of the appended claims.

What is claimed is:

1. A method for measuring a vertical density profile of a fluid in a fluid storage tank by using an array of open-ended upright pressure pipes, which pipes extend downward into said fluid, each said pipe having at its upper end means for connecting to a common pressurizing gas supply and said pipe having at its lower end a fluid level sensor head, the method comprising the following sequence of steps, carried out for each pipe:
   connecting said pipe with said common gas supply,
   conducting the pressurizing gas into said pipe thereby forcing the fluid downward into said fluid level sensor head, said sensor head comprising a lower end part in which the fluid passes an outlet opening forming an abrupt transition between said lower end part and an open ended tube,
   determining a level-indicating signal of the passing fluid,
   determining a pressure-indicating signal of the pressure on the fluid, and
   deriving a vertical density profile of said fluid from said level-indicating and pressure-indicating signals.

2. A system for measuring a vertical density profile of a fluid in a fluid storage tank by means of an array of open-ended upright pressure pipes each pipe extending downward to a different depth in said fluid, the top end of each said pressure pipe having means for connecting with a common pressurizing gas supply, and the bottom end of said pressure pipe having a fluid level sensor head, the system comprising at least two pipes, each said pipe having
   means for connecting said pipe with the common gas supply,
   means for conducting the pressurizing gas into said pipe thereby forcing the fluid downward into a fluid level sensor head mounted at the lower end of said pipe, said head comprising a chamber having a horizontal cross-sectional area larger than said pipe and having a lower end part in which the fluid passes through an outlet having an opening of smaller horizontal cross-sectional area than said chamber between said lower end part and an open ended tube,
   means for determining a level-indicating signal from the passing fluid,
   means for determining a pressure-indicating signal from the pressure on the fluid, and
   means for deriving from said level-indicating and pressure-indicating signals information on said vertical density profile.

3. A fluid level sensor head comprising an inlet opening, connected with a pressure pipe as a conduit for fluid forced downward by means of a pressurizing gas, a chamber disposed below said pipe having a horizontal cross-sectional area larger than said pipe and disposed below said chamber a lower end part, provided with an outlet opening having a smaller cross-sectional area than said chamber, thereby forming an abrupt transition between said lower end part and an open ended tube, each said pressure pipe, chamber and open-ended tube having an axis.

4. The fluid level sensor head as in claim 3 wherein said chamber on the lower end part is a tube having a diameter substantially greater than the diameter of said open ended tube.

5. The fluid level sensor head as in claim 3 wherein said outlet opening is comprised in a flat bottom connecting the lower end part with the open ended tube and normal to the axes of said tubes.

6. The fluid level sensor head as in claim 4 wherein said chamber is a tubular room, having an inlet opening diameter smaller than the diameter of said tubular room.

7. The fluid level sensor head as in claim 6 wherein the inlet opening is comprised in a flat top connecting said tubular room with the pressure pipe and normal to the axes of said room and said pressure pipe.

8. The fluid level sensor head as in claim 3 wherein said pressure pipe, said lower end part and said open ended tube are arranged coaxially.

* * * * *